(12) United States Patent
Cassingham et al.

(10) Patent No.: US 8,802,146 B2
(45) Date of Patent: *Aug. 12, 2014

(54) SYSTEMS, METHODS, AND COMPOSITIONS FOR PREVENTION OF TISSUE ADHESION

(75) Inventors: Charles Vaughn Cassingham, Newport Beach, CA (US); William Jerome Mezger, Coto De Caza, CA (US)

(73) Assignee: Neomend, Inc., Irvine, CA (US)

( * ) Notice: Subject to any disclaimer, the term of this patent is extended or adjusted under 35 U.S.C. 154(b) by 469 days.

This patent is subject to a terminal disclaimer.

(21) Appl. No.: 11/716,266

(22) Filed: Mar. 9, 2007

(65) Prior Publication Data

US 2007/0213683 A1    Sep. 13, 2007

Related U.S. Application Data

(63) Continuation-in-part of application No. 10/141,510, filed on May 8, 2002, now Pat. No. 7,279,001, which is a continuation-in-part of application No. 09/780,843, filed on Feb. 9, 2001, now Pat. No. 6,949,114, which is a continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(51) Int. Cl.
*A61K 9/14* (2006.01)

(52) U.S. Cl.
USPC ........................................................ 424/486

(58) Field of Classification Search
None
See application file for complete search history.

(56) References Cited

U.S. PATENT DOCUMENTS

| | | | |
|---|---|---|---|
| 4,179,337 A * | 12/1979 | Davis et al. | 435/181 |
| 4,786,421 A | 11/1988 | Butterworth et al. | |
| 5,786,421 A * | 7/1998 | Rhee et al. | 525/54.1 |
| 6,371,975 B2 * | 4/2002 | Cruise et al. | 606/214 |
| 7,279,001 B2 * | 10/2007 | Addis et al. | 606/214 |
| 2002/0064546 A1 * | 5/2002 | Harris | 424/426 |
| 2003/0100921 A1 | 5/2003 | Addis et al. | |
| 2005/0214902 A1 | 9/2005 | Belew et al. | |
| 2006/0024371 A1 | 2/2006 | Hnojewyj et al. | |
| 2010/0099852 A1 | 4/2010 | Cassingham et al. | |

FOREIGN PATENT DOCUMENTS

| | | | |
|---|---|---|---|
| JP | 2006-83396 A * | 3/2006 | |
| WO | WO 01/66017 A1 | 9/2001 | |
| WO | WO 02/102864 A1 | 12/2002 | |

OTHER PUBLICATIONS

English abstract of JP 2006-83396 A, Mar. 2006.*
Supplementary European Search Report dated Jul. 31, 2012 for EP 08725938.
Office Action dated Jan. 29, 2013 for corresponding Japanese Application No. 2009-553579.

* cited by examiner

*Primary Examiner* — Paul Dickinson
(74) *Attorney, Agent, or Firm* — Pepper Hamilton LLP

(57) ABSTRACT

A blended electrophilic material with a first component having a functionality of at least three and a second component having a functionality of two is mixed with a nucleophilic material. The blended electrophilic material cross-links with the nucleophilic material to form a non-liquid, three dimensional structure which can applied, e.g., as an adhesion barrier.

14 Claims, 3 Drawing Sheets

SYSTEMS, METHODS, AND COMPOSITIONS FOR PREVENTION OF TISSUE ADHESION

RELATED APPLICATIONS

This application is a continuation-in-part of co-pending U.S. patent application Ser. No. 10/141,510, filed May 8, 2002, entitled "Systems, Methods, and Compositions for Achieving Closure of Vascular Puncture Sites" (now U.S. Pat. No. 7,279,001), which is a continuation-in-part of U.S. patent application Ser. No. 09/780,843, filed Feb. 9, 2001, entitled "Systems, Methods, and Compositions for Achieving Closure of Vascular Puncture Sites" (now U.S. Pat. No. 6,949,114), which is a continuation-in-part of U.S. patent application Ser. No. 09/283,535, filed Apr. 1, 1999, entitled "Compositions, Systems, And Methods For Arresting or Controlling Bleeding or Fluid Leakage in Body Tissue" (now U.S. Pat. No. 6,458,147), which is itself a continuation-in-part of U.S. patent application Ser. No. 09/188,083, filed Nov. 6, 1998, entitled "Compositions, Systems, and Methods for Creating in Situ, Chemically Cross-linked, Mechanical Barriers" (now U.S. Pat. No. 6,371,975), all of which are incorporated herein by reference.

FIELD OF THE INVENTION

The invention generally relates to systems, methods and composition of biocompatible materials and their application to body tissue to affect desired therapeutic results.

BACKGROUND OF THE INVENTION

Adhesion formation following surgery or trauma is generally considered to be undesirable. For example, adhesions that form in relation to intestinal surgery, e.g., bowel resection, hernia repair, etc. may cause obstruction of the intestine. Adhesions that form near the bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function.

Hydrogel materials that may serve well as wound sealants, e.g., possessing a high strength and degradation resistance during the wound healing time frame (approximately 5-10 days), may not serve well as adhesion barriers, which should degrade relatively quickly. However, hydrogel materials that provide relatively rapid degradation may also possess a gel strength that is relatively weak. Balancing these two qualities—high gel strength and rapid degradation—poses a technical challenge.

SUMMARY OF THE INVENTION

Systems, methods, and compositions are described that comprise a blended electrophilic material with a first component having a functionality of at least three and a second component having a functionality of two. The blended electrophilic material cross-links with a nucleophilic material, to form a non-liquid, three dimensional structure, or hydrogel. The structure can serve, e.g., as an adhesion barrier. The structure provides sufficiently strong gel strength over a reasonable adhesion formation period, to serve as an adhesion barrier, yet it still dissolves within a reasonable quick time period after there is need for an adhesion barrier is gone.

Features and advantages of the inventions are set forth in the following Description and Drawings, as well as in the appended Claims.

Figure 1:
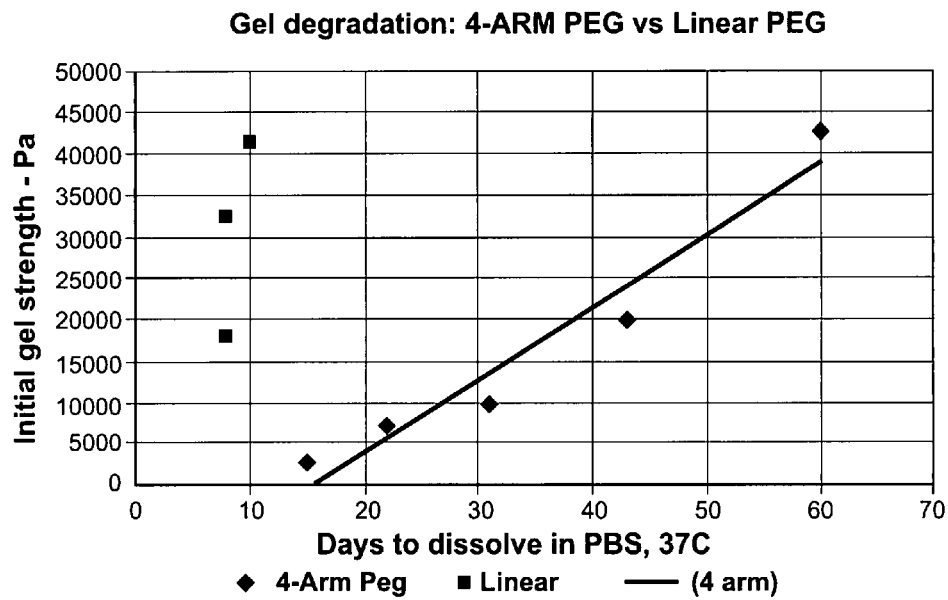
FIG. 1 is a graphical representation comparing the gel strength and gel degradation of a hydrogel structure comprising a multi-functional PEG to a hydrogel structure comprising a linear PEG.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

I. Adhesion Barrier Composition

A composition is described that is well suited for use in various biological procedures, and in particular, providing an adhesion barrier. The composition comprises a blended electrophilic material, which is mixed with a nucleophilic material and a buffer material. When mixed, the blended electrophilic and nucleophilic materials react by cross-linking, forming a three dimension, non-liquid hydrogel structure.

Each of the materials will now be separately described.

A. The Blended Electrophilic Material

The electrophilic material comprises a blend including a first hydrophilic biocompatible component with a functionality of at least three (i.e. in shorthand, the first component is "multi-functional") and a second biocompatible component having a functionality of two (i.e. in shorthand, the second component is "linear" or "bi-functional"). The blended material can also be called a "hybrid" material, because it includes both a linear (bi-functional) component and non-linear (multi-functional) component (possessing three functional groups or greater) present in the blend.

One or both linear and non-linear components can comprise a synthetic polymer. For example, one or both of the first and second components portions can comprise poly(ethylene glycol), poly(ethylene oxide), poly(vinyl alcohol), poly(vinylpyrrolidinone), poly(ethyloxazoline), and poly(ethylene glycol)-co-poly(propylene glycol) block copolymers, having the appropriate structure (linear or non-linear). Alternatively, one or both of the first and second components can comprise a non-synthetic electrophilically derivatized material. For example, polysaccharides, carbohydrates, and proteins could be electrophilically derivatized with either a functionality of at least three and a linear functionality.

Still alternatively, proteins with one or more substitutions, deletions, or additions in the primary structure may be used as the first and/or second components. In this arrangement, the protein's primary structure is not restricted to those found in nature, as an amino acid sequence can be synthetically designed to achieve a particular structure and/or function and then incorporated into the material. The protein can be recombinantly produced or collected from naturally occurring sources.

Each of the multifunctional and linear materials will now be separately described.

(i) Multi-Functional Electrophilic Component

In a representative embodiment, the first polymer component comprises a multi-functional poly(ethylene glycol) (PEG) material with a molecular weight preferably between 9,000 and 12,000, and most preferably 10,500±1500. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of solutions, but sterile water is preferred.

The most preferred multi-functional PEG material can be generally expressed as compounds of the formula:

$$\text{PEG-(DCR-CG)}_n$$

Where:
DCR is a degradation control region.
CG is a cross-linking group.
$n \leq 3$ The electrophilic CG is responsible for the cross-linking of the nucleophilic material, as well as binding the composition to the like material in the surrounding tissue. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate.

The preferred CG's are active esters, more preferred, an ester of N-hydroxysuccinimide. The active esters are preferred since they react rapidly with nucleophilic groups and have a non-toxic leaving group, e.g., hydroxysuccinimide.

The selection of a particular CG can be dependent on which component (multi-functional or linear) of the hybrid material comprises the majority of the hybrid material. For example, an hydroxysuccinimide, such as succinimydyl succinate may be the CG when the linear component of the hybrid material is prevalent. Succinimidyl glutarate may be the selected CG when the multi-functional component is prevalent in the hybrid material. However, it is understood that various compounds described above could be used in combination.

The concentration of the CG in the polymer material can be used to control the rate of gelation. However, changes in this concentration typically also result in changes in the desired mechanical properties of the hydrogel.

The hydrogel is also desirably capable of transforming over time by physiological mechanisms from the solid state to a biocompatible liquid state, which can be cleared by the body, in a process called "degradation." The rate of degradation is controlled by the degradation control region (DCR), the concentration of the CG's in the polymer material, and the concentration of the nucleophilic groups in the nucleophilic material. Changes in these concentrations also typically result in changes in the mechanical properties of the hydrogel, as well as the rate of degradation.

The rate of degradation is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly(glycolic acid), poly(DL-lactic acid), poly(L-lactic acid), poly(ξ-caprolactone), poly(δ-valerolactone), poly(γ-butyrolactone), poly(amino acids), poly (anhydrides), poly(orthoesters), poly(orthocarbonates), and poly(phosphoesters), and derivatives thereof. A preferred hydrolytically degradable DCR is gluturate. Examples of enzymatically degradable DCRs include Leu-Gly-Pro-Ala (collagenase sensitive linkage) and Gly-Pro-Lys (plasmin sensitive linkage). It should also be appreciated that the DCR could contain combinations of degradable groups, e.g. poly (glycolic acid) and di-acid.

A preferred starting multi-functional polymer material may be purchased from Shearwater Polymers. Inc. (Product Designation: PEG4SG, having a molecular weight range of between 9000 and 12,000) (which will be called the "Shearwater PEG"). Gel permeation chromatography of the Shearwater PEG reveals that (by molecular weight) 59.2% of the Shearwater PEG comprises 4-Arm-PEG polymer.

Alternatively, another preferred starting multi-functional polymer material may be purchased from SunBio Company (P4SG10) having a molecular weight of 10,500±1500) (which will be called the "SunBio PEG"). Gel permeation chromatography of the SunBio PEG reveals that (by molecular weight) 3.1% of the SunBio PEG comprises 3-Arm-PEG polymer and 90.7% of the SunBio PEG comprises 4-Arm-PEG polymer.

(ii) Linear Electrophilic Component

The second component of the blended polymer material comprises a linear or bifunctional PEG material having a molecular weight between 1,000-15,000 and more preferably in the range of 2,000-4,000, with a most preferred molecular weight being 3,400±600. The linear PEG material may be one of any commercially available materials.

The most preferred linear PEG material can be generally expressed as compounds of the formula:

$$\text{PEG-(DCR-CG)}_n$$

Where:
DCR is a degradation control region.
CG is a cross-linking group.
n=2

Selection or the electrophilic CG and DCR for the linear PEG material is governed by the considerations of selection set forth above for the multi-functional PEG material.

Both multi-functional and linear PEG components can react with water (i.e., hydrolyze), thereby losing the ability to react with the nucleophilic component. For this reason, the blended material is desirably stored dry before use and dissolved under conditions where it does not hydrolyze rapidly. The storage container for the blended material desirably is evacuated by use of a vacuum, and the blended material is stored therein under an inert gas, such as Argon or Nitrogen. Another method of packaging the blended material is to lyophilize the blended material and store it under vacuum, or under an inert gas, such as Argon or Nitrogen. Lyophilization provides the benefits of long term storage and product stability, as well as allows rapid dissolution of the blended material in water.

B. Nucleophilic Component

As stated above, the hybrid material is mixed or combined with a nucleophilic material.

In one embodiment, the nucleophilic material comprises a non-immunogenic, hydrophilic protein. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the nucleophilic material. The protein can be recombinantly produced or collected from naturally occurring sources.

A representative protein solution is 25% human serum albumin, USP or less, more preferably 20% or less, and most preferably—about 15% human serum albumin. A preferred ratio of albumin to the hybrid polymer material is approximately 6.5:1 hybrid polymer material/albumin. Human serum albumin is preferred due to its biocompatibility and its ready availability.

When mixed under proper reaction conditions (as will be described below), the blended electrophilic material and nucleophilic material react, by cross-linking with each other. The cross-linking of the materials forms a three dimensional, mechanical barrier, which can also be characterized as a hydrogel. The rate at which cross-linking reaction occurs to form a gel that possesses sufficient cohesive and adhesive strength to form an adhesion barrier establishes what is called the "gelation time."

C. The Buffer Component

The first and second materials are desirably mixed in conjunction with a buffer material.

The conditions that speed up the reaction with protein, described above, include increased temperature; increased concentration; and increased pH (i.e., increased alkali). In the context of adhesion prevention, in situ temperature cannot be easily varied, so varying the concentrations and the pH are the primary methods of control.

It is the purpose of the buffer material to establish an initial pH to achieve a desired gelation time, and to sustain the pH as added acid is produced by the release of N-hydroxysuccinimide during cross linking and hydrolysis.

Phosphate, tris-hydroxymethylaminomethane (Tris), bicarbonate, and carbonate are all non-toxic, biocompatible buffers. One preferable buffer is a bicarbonate material having a concentration of approximately 100 mM to 300 mM and operating in a pH range of about 8-11. Phosphate provides increased buffering capacity to albumin at pH's up to about 8.5. Tris provides increased buffering capacity to albumin at pH's up to about 9.5. Addition of Tris to albumin (Plasbumin) at a concentration of 60 mM approximately doubles the buffering capacity of the albumin at a pH near 9. Carbonate provides increased buffering capacity to albumin in the higher pH ranges. Depending upon the gelation time that is targeted, formulations of Tris, carbonate, bicarbonate and albumin can be used for the buffer material.

II. The Adhesion Barrier Composition

As described above, the multi-functional electrophilic PEG component is blended with the linear electrophilic PEG component, creating the hybrid PEG electrophilic material. The hybrid PEG electrophilic material is then mixed with the nucleophilic protein material in the presence of the buffer material.

The blended or hybrid PEG polymer material can be of any weight ratio or range between the first component and the second component. Preferably, the weight ratio w/w % will between about 10% to 90% w/w for the first component, and, correspondingly, about 90% to 10% w/w for the second component. In one representative embodiment, the first component and the second component each comprise about 50% (±20%) w/w of the electrophillic material (i.e., about a 1:1 weight ratio).

In one representative embodiment, a hybrid or blended polymer material comprises a first component having a PEG compound having a 4-arm functionality (i.e., 60% w/w) and a second component having a PEG compound having a linear functionality (i.e., 40% w/w). In this embodiment, the ratio of 4-arm functionality to linear functionality is approximately about 1:2. The individual molecular weight of the linear second component is approximately 3400, and the individual molecular weight of the 4-arm first component is approximately 10,000. The hybrid or blended polymer material is mixed with a buffered albumin material at a 6.5:1 ratio. The resultant composition will generally have a concentration of approximately 0.03 mM for the linear second component and approximately 0.015 for the 4-arm first component.

The blended or hybrid PEG electrophilic material reacts with the amino groups of the nucleophilic protein material and other tissue proteins that may be present in situ, with the release of N-hydroxysuccinimide and the formation of a link between the PEG material (both multi-functional and linear components) and the protein material. When there are multiple reactive ester groups per PEG molecule, and each protein has many reactive groups, a network of links form, binding all the albumin molecules to each other and to adjacent tissue proteins. This degree of cross-linking occurs during the so-called gelation time.

The buffer material establishes an initial pH to achieve a desired gelation time, and sustains the pH as added acid is produced by the release of N-hydroxysuccinimide during cross linking and hydrolysis. To minimize the liberation of heat during the cross-linking reaction, the concentration of the cross-linking groups (CG) of the fundamental polymer component is preferably kept less than 5% of the total mass of the reactive solution, and more preferably about 1% or less. The low concentration of the cross-linking group (CG) is also beneficial so that the amount of the leaving group is also minimized. In a typical clinical application, about 14 mg of a non-toxic leaving group is produced during the cross-linking reaction, a further desired result. In a preferred embodiment, the CG comprising an N-hydroxysuccinimide ester has demonstrated ability to participate in the cross-linking reaction with albumin without eliciting adverse immune responses in humans.

The use of blended or hybrid PEG polymers as above described provide a surprising advantage when albumin is used as the nucleophilic material. When cross-linked with hybrid PEG polymers, the concentration of albumin can be reduced to 25% and below. Past uses of solely bifunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

The composition comprising a blended or hybrid polymer material as above described possesses a desirably high gel strength (GS) through the entire wound healing time frame (approximately 5-10 days), with an initially resistance to degradation. It has been determined that the composition comprising a blended or hybrid polymer material as above described possesses an initial strength of at least about 15,0000 Pa, to achieve wound sealing and tissue adhesiveness. The gel strength remains above about 5,000 Pa for at least ten days, or through the entire wound healing time frame, as well as the adhesion formation time frame.

At the same time, the composition comprising a blended or hybrid polymer material as above described acts as a good adhesion barrier, because the gel eventually degrades relatively quickly within the adhesion formation time frame of approximately 0 to 10 days. It has been determined that the composition comprising a blended or hybrid polymer material as above described quickly loses strength after ten days and is dissipated entirely from the system within thirty days.

Such rapid hydrolysis is generally not achievable when only multi-functional PEG groups are present, as each of the functional groups presents a cross-link that must be broken. This is why multi-functional groups do not form adequate adhesion barriers alone. The composition comprising a blended or hybrid polymer material, including both multi-function as well as liner PEG groups, as above described achieves more rapid hydrolysis, and makes the composition well suited for use as an adhesion barrier.

EXAMPLE

The above description is only one possible combination and blend of materials. Table 1 shows results of in vitro and in vivo tests, comparing different degradation rates of various multi-functional PEG sample materials (Materials 1 to 5), linear PEG materials (Materials 6 to 8), and blended or hybrid PEG materials (Materials 9 to 20).

TABLE 1

PEG Degradation Comparisons

| Initial Conditions | PEG functionality | Albumin in % | PEG/Albumin Ratio | Initial Gel Strength | Days Until Dissolved |
|---|---|---|---|---|---|
| Material 1 | 100% 4-Arm | 25 | 5.3 | 43170 | 60 |
| Material 2 | 100% 4-Arm | 12.5 | 5.3 | 19970 | 43 |
| Material 3 | 100% 4-Arm | 9.4 | 5.3 | 6931 | 22 |
| Material 4 | 100% 4-Arm | 9.4 | 3.5 | 2768 | 15 |
| Material 5 | 100% 4-Arm | 9.4 | 7 | 9870 | 31 |
| Material 6 | 100% Linear | 40 | 5.6 | 32388 | 8 |
| Material 7 | 100% Linear | 25 | 5.3 | 18070 | 8 |
| Material 8 | 100% Linear | 25 | 10.5 | 41370 | 10 |
| Material 9 | 90% 4-Arm | 10 | 7.5 | 17720 | 12 |
| Material 10 | 90% 4-Arm | 17.5 | 5.5 | 34440 | 15 |
| Material 11 | 90% 4-Arm | 20 | 3.5 | 25100 | 13 |
| Material 12 | 50% 4-Arm | 10 | 7.5 | 11100 | 8 |
| Material 13 | 50% 4-Arm | 17.5 | 5.5 | 29720 | 12 |
| Material 14 | 50% 4-Arm | 10 | 5.5 | 6060 | 8 |
| Material 15 | 50% 4-Arm | 20 | 3.5 | 19100 | 8 |
| Material 16 | 50% 4-Arm | 15 | 3.5 | 10000 | 9 |
| Material 17 | 25% 4_arm | 17.5 | 7.5 | 34850 | 13 |
| Material 18 | 25% 4_arm | 17.5 | 7.5 | 21850 | 7 |
| Material 19 | 25% 4_arm | 17.5 | 5.5 | 13200 | 5 |
| Material 20 | 25% 4_arm | 17.5 | 3.5 | 7935 | 4 |

Figure 2:
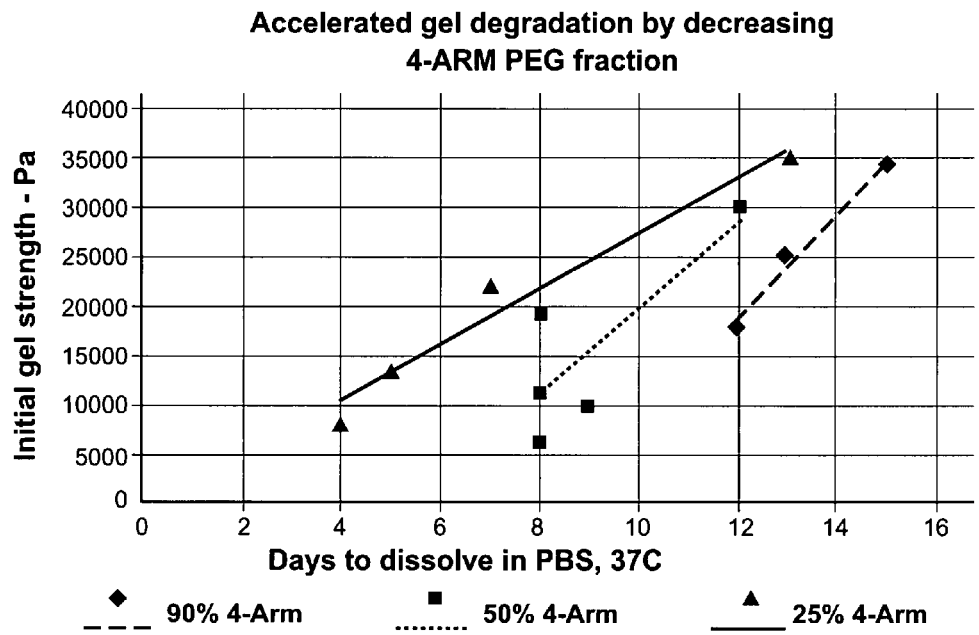
FIG. 2 is a graphical representation comparing the gel strength and gel degradation rates of various hybrid PEG gels that comprise a first PEG component having a functionality of at least three and a second PEG component having a functionality of two.

Further comparisons of the compounds from Table 1 are compared in the graph of FIGS. 1 and 2. FIG. 1 compares the rate of degradation between multi-functional PEG groups (4-arm groups or having four functionality groups) (Materials 1-5, Table 1) and linear or bifunctional PEG groups (Materials 6-8, Table 1). The gel strength (GS) of each material in Pascals (Pa) is compared with the number of days the gel is in a phosphate buffered saline (PBS). As is demonstrated, the 100% linear PEG degrades too rapidly, i.e. dissolves in less than ten days, while the 100% multi-functional PEG tends to stay in the body for an undesirable amount of time, which can potentially be upwards to 60 days depending on the concentration of the initial gel strength. Also, the correlation between the initial gel strength of the multi-functional PEG material compared to the number of days required for the gel to dissolve is generally a linear correlation. That is, as the initial gel strength of the multi-functional material increases, the number of days for the material to dissolve increases in a relatively linear fashion, as well.

FIG. 2 compares various hybrid PEG materials composed of different amounts of multi-functional PEG. In FIG. 2, a hybrid PEG material comprising 90% multi-functional PEG material (Materials 9-11, Table 1) is compared to hybrid PEG materials comprising 50% multi-functional PEG material (Materials 12-16, Table 1) and 25% multi-functional PEG material (Materials 17-20, Table 1). Each of the materials is plotted as in FIG. 1, with the initial gel strength (Pa) plotted against the time for the material to dissolve (days). Each of the materials generally portrays a linear correlation of gel strength vs. time, which can be further used for selecting material blends for specific uses. As shown, the hybrid PEG material does have the potential to meet the results discussed above: an initial strength of 15,000 or more Pa, a level of 5,000 or more Pa for 10 days, and removal from the system within 30 days, with all of the materials of FIG. 2 being removed from the system within 15 days.

The blended or hybrid PEG materials (Materials 9 to 20, Table 1) provided surprising results for the use in forming an adhesion barrier. The balance of having an initial material strength of at least 15,000 Pa, a strength of 5,000 Pa for at least 10 days, and dissipation from the system within 30 days was not previously realized by previous linear and multi-functional PEG materials. Furthermore, it was not contemplated to combine linear and multi-functional PEG materials as they generally had attributes that were not necessarily compatible. For instance, while linear PEG compositions generally have been used for adhesive sealant composition, they have not been used for wound sealants. Similarly multi-functional PEG compounds have been used for wound sealant compositions, but they have not been used as adhesive sealant compositions. Thus, the ability to combine the differing PEG functionality components into one effective material having both adhesive sealant and wound sealant attributes is a great improvement over the known art.

III. Delivering of the Materials to Form an Adhesion Barrier

The adhesion barrier composition can be applied to a biological surface, preferably by spraying. The following is an example of a device that can be used to dispense the present materials.

Figure 3:
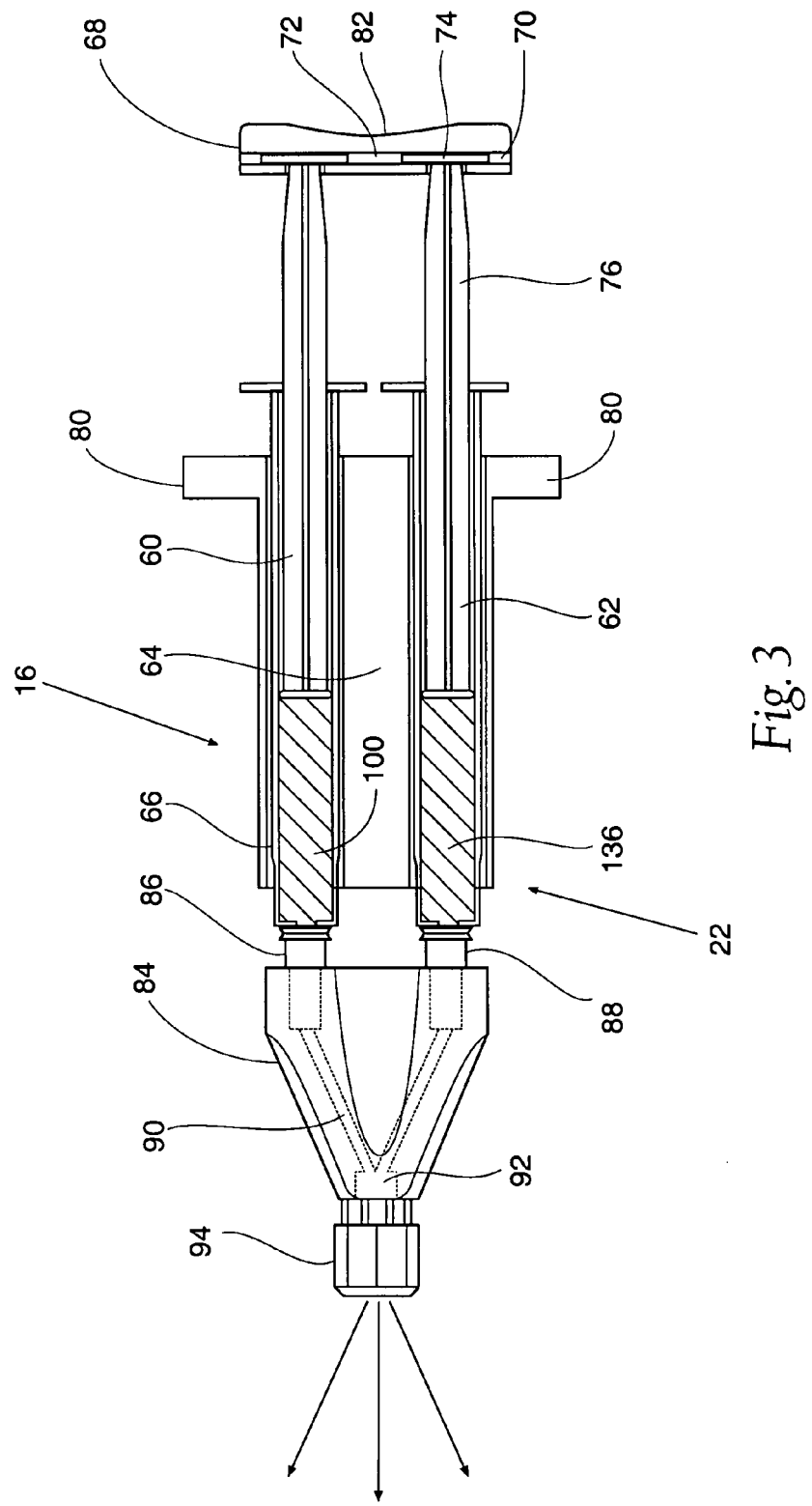
FIG. 3 is a side view, with portion broken away and in section, of an embodiment of a device for mixing a nucleophilic material with an electrophilic material, which comprises a blend of a first component having a functionality of at least three and a second component having a functionality of two, and for spraying the mixture on a tissue site.

As FIG. 3 shows, a dispersing assembly 16 comprises a material introducer/mixer 22. The material introducer/mixer 22 receives the two dispensing syringes 60 and 62. The syringe 60 holds the hybrid or blended PEG material, with a buffered diluent that has been added at the time of use. The syringe 62 holds the protein material in liquid state. The material introducer/mixer 22 allows the physician to uniformly dispense the two materials in the two syringes 60 and 62 in a liquid state from the dispensing syringes 60 and 62, statically mixing them together.

To accomplish these functions (see FIG. 3), the material introducer/mixer 22 includes syringe support 64. The support 64 includes side-by-side channels 66 (see FIG. 1, too). The channel 66 accommodates in a snap-friction-fit the barrels of the syringes 60 and 62.

The material introducer/mixer 22 also includes a syringe clip 68. The syringe clip 68 includes spaced apart walls 70 forming an interior race 72. The race 72 receives in a sliding friction fit the thumb rests 74 of the pistons 76 of the dispensing syringes 60 and 62, in axial alignment with the syringe barrels carried by the syringe support 64. The syringe clip 68 mechanically links the syringe pistons 76 together for common advancement inside their respective syringe barrels.

To facilitate handling, the syringe support 64 includes opposed finger rests 80, and the syringe clip 68 includes a thumb rest 82. The orientation of these rests 80 and 82 parallel the orientation of the finger rests and thumb rests of a single syringe. The physician is thereby able to hold and operate multiple syringes 60 and 62 in the same way as a single syringe.

The material introducer/mixer 22 also includes a joiner 84. The joiner 84 includes side by side female LUER® fittings 86. The female LUER® fittings 86 each receives the threaded male LUER® fitting 88 at the dispensing end of the dispensing syringes 60 and 62. The female LUER® fittings 86 are axially aligned with the barrels 78 of the dispensing syringes 60 and 62 carried in the syringe support 64.

The physician is thereby able to quickly and conveniently ready the dispensing syringes 60 and 62 for use by securing the dispensing syringes to the joiner 84, snap fitting the syringe barrels 78 into the syringe support 64, and slide fitting the syringe thumb rests 74 into the clip 68.

The joiner 84 includes interior channels 90 coupled to the female LUER® fittings 86. The channels 90 merge at a Y-junction into a single outlet port 92. The joiner 84 maintains two fluids dispensed by the syringes 60 and 62 separately until they leave the joiner 84. This design minimizes plugging of the joiner 84 due to a mixing reaction between the two fluids. The syringe clip 68 ensures even application of individual solutions through the joiner 84.

The material introducer/mixer 22 further includes a mixing spray head 94, which, in use, is coupled to the single outlet port 92. The introducer/mixer is capable of being used with several interchangeable mixing spray heads 94, in case one mixing spray head 94 becomes clogged during use.

The mixing spray head 94 may be variously constructed. It may, for example, comprise a spray head manufactured and sold by Hemaedics.

Figure 4:
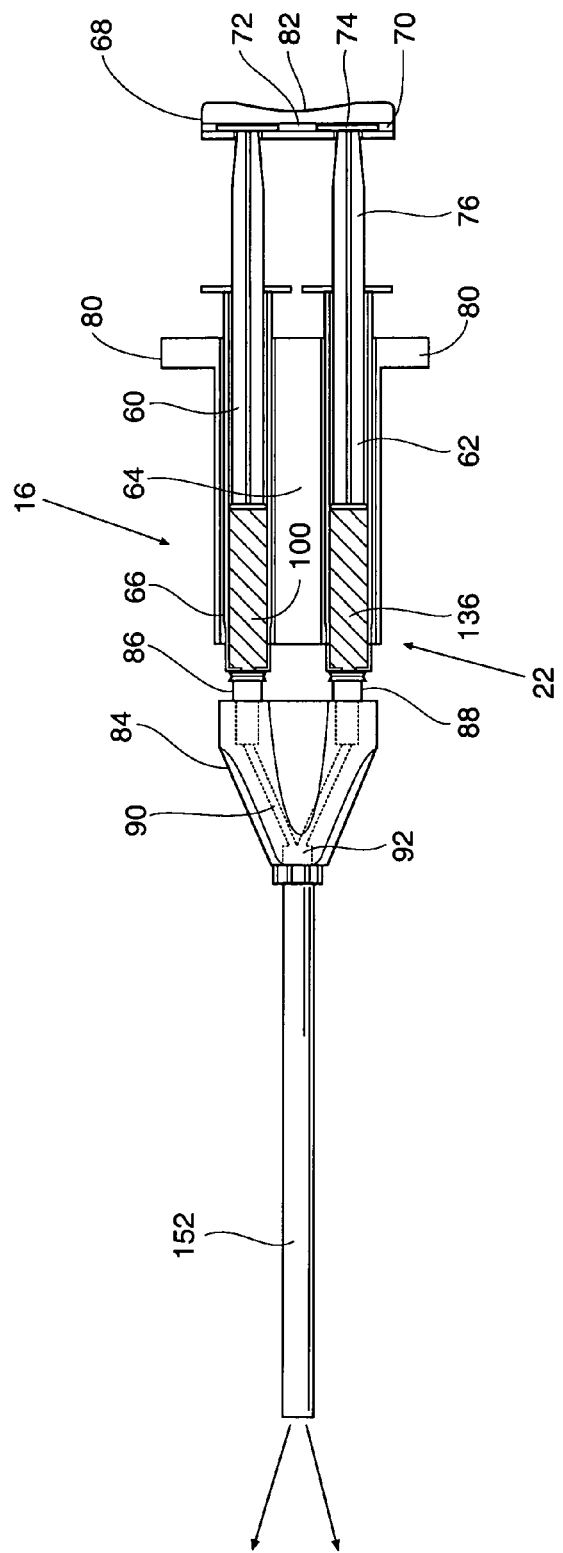
FIG. 4 is a side view, with portions broken away and in section, of another embodiment of a device for mixing a nucleophilic material with an electrophilic material, which comprises a blend of a first component having a functionality of at least three and a second component having a functionality of two, and for spraying the mixture on a tissue site.

Alternatively, the material introducer/mixer 22 can include a cannula 152, which, in use, can be coupled to the outlet port 92 instead of the mixing spray head (see FIG. 4).

Expressed in tandem from the dispensing syringes 60 and 62, which are mechanically linked together by the joiner 84, support 64, and clip 68, the two components of the barrier material come into contact in the liquid state either in the mixing spray head 94 or the cannula 152. Atomization of the two components occurs as they are dispersed through the mixing spray head 94 under pressure from operation of the mechanically linked dispensing syringes 60 and 62. Passage of the liquid components through the cannula 152 will channel-mix the materials. Either by atomization or channel mixing, the liquid components are sufficiently mixed to immediately initiate the cross-linking reaction.

The parts of the introducer/mixer 22 are made, e.g., by molding medical grade plastic materials, such as polycarbonate and acrylic.

Thus, the present invention provides an improved composition that is capable of providing an adhesion barrier, and also has wound sealant capabilities. Depending on the specific use for the composition, the ratio of multi-functional component of the hybrid material to the linear component of the hybrid material can be altered.

The features of the invention are set forth in the following claims.

What is claimed is:

1. A method comprising:
   providing a blended electrophilic material comprising a first poly(ethylene glycol) PEG component having a functionality of at least three and a second PEG component having a functionality of two;
   providing a nucleophilic material, separate from the blended electrophilic material, which upon mixing with the blended electrophilic material, cross-links with the blended electrophilic material to form a non-liquid, three dimensional structure; and
   mixing the blended electrophilic material and the nucleophilic material to form the non-liquid, three dimensional structure.

2. A method according to claim 1, wherein the non-liquid, three dimensional structure forms upon tissue.

3. A method according to claim 2, wherein the non-liquid, three dimensional structure comprises an adhesion barrier.

4. A method according to claim 1, wherein the blended electrophilic material comprises a first component having a PEG compound having a 4-arm functionality and a second component having a PEG compound having a linear functionality.

5. A method according to claim 4, wherein the PEG compound having 4-arm functionality comprises about 60% w/w of the blended electrophilic material.

6. A method according to claim 4, wherein the PEG compound having linear functionality comprises about 40% w/w of the blended electrophilic material.

7. A method according to claim 1, wherein said nucleophilic material comprises a protein, which is from a natural source.

8. A method according to claim 1, wherein the first PEG component comprises between 10% to 90% w/w of the blended electrophilic material.

9. A method according to claim 1, wherein the first PEG component has a functionality of four.

10. A method according to claim 1, wherein the first PEG component comprises about 50% w/w of the blended electrophilic material.

11. A method according to claim 1, further including a buffer material.

12. A method according to claim 7, wherein the protein comprises natural serum albumin.

13. A method according to claim 12, wherein the natural serum albumin is at a concentration of 25% or less.

14. A method according to claim 12, wherein the natural serum albumin is at a concentration of about 15%.

* * * * *